United States Patent [19]

Sonnenberg

[11] 4,002,645
[45] Jan. 11, 1977

[54] BIS AROMATIC ANHYDRIDES
[75] Inventor: Joseph Sonnenberg, San Jose, Calif.
[73] Assignee: Raychem Corporation, Menlo Park, Calif.
[22] Filed: May 31, 1974
[21] Appl. No.: 475,050

Related U.S. Application Data
[63] Continuation-in-part of Ser. No. 123,036, March 10, 1971, abandoned.

[52] U.S. Cl. .......................... 260/345.2; 260/315; 260/329.3; 260/346.2 M; 260/346.3; 260/516; 260/517
[51] Int. Cl.² ....................................... C07D 307/89
[58] Field of Search ............ 260/346.3, 315, 329.3, 260/345.2, 346.2 M

[56] References Cited
FOREIGN PATENTS OR APPLICATIONS
1,565,700  5/1969  France
2,211,327  6/1973  Germany OTHER PUBLICATIONS
Drechsler et al., Journal fur Praktische Chemie, vol. 27(4), pp. 152–165 (1965).
Gilman et al., J.A.C.S. vol. 61, pp. 2836–2841 (1939).

Primary Examiner—Henry R. Jiles
Assistant Examiner—Bernard Dentz
Attorney, Agent, or Firm—Lyon & Lyon

[57] ABSTRACT

Novel bis-anhydrides are obtained by, for example, ferric chloride-catalyzed Friedel-Crafts reactions with polynuclear aromatic compounds and the monoacid halide of trimellitic anhydride. Melt-processable polyimides exhibiting good mechanical properties are prepared from the bis-anhydrides.

24 Claims, No Drawings

BIS AROMATIC ANHYDRIDES

CROSS REFERENCE TO RELATED APPLICATIONS

This is a continuation-in-part of copending application, Ser. No. 123,036 filed Mar. 10, 1971 now abandoned.

BACKGROUND OF THE INVENTION

Polyimides are finding wide and increasing use in various fields of industry, especially as electrical insulation and, more recently, as structural materials. The advantages of polyimides are widely known, among them being the relatively high temperatures at which they may be used, their good electrical properties and high mechanical strength. Many suffer, however, from the disadvantage of requiring fabrication from a precursor, usually the polyamic acid, since the polyimide itself is intractable. This limits the size of articles which can be manufactured because water resulting from the conversion to the final product must be allowed to escape. A small number of specialty moldable polyimides are available, but, due to expensive starting materials and difficult processing techniques, they are quite high in price.

Because of these disadvantages, many efforts have been made to modify the polyimide structure to render it more tractable. Among these efforts are the introduction into the molecule of "hinges" which render the material more processable or the introduction of some group other than the imide, such as an ester or an amide link.

Thus, after the basic polymers disclosed in British Pat. No. 570,858 and U.S. Pat. Nos. 3,179,614, 3,179,630 to 3,179,634, it has been proposed as in U.S. Pat. No. 3,231,181 to manufacture a "malt-fabricable" polyimide derived from a diamine and bis-anhydride, each of which contains a pair of aromatic rings separated by a divalent bridging group, i.e., containing carbon, nitrogen, oxygen, silicon, phosphorus, or sulphur. In each case, a single atom bridges the rings. In U.S. Pat. No. 3,190,856 the use of benzophenonetetracarboxylic acid dianhydrides is proposed. Koton et al (J.Org.Chem., USSR 4, 754 (1968) disclose somewhat complicated routes to bis-anhydrides containing other linkages. More complex linkages between the aromatic rings carrying the anhydride moieties have been achieved by the use of trimellitic and similar anhydrides, as disclosed in U.S. Pat. No. 3,182,073, in which two molecules of the anhydride of a tricarboxylic acid react with one molecule of a difunctional amine, phenol, thiol, or compound containing a combination of two such functions.

The disclosure of the above-mentioned patents is incorporated herein by reference.

While the polyesterimides or polyamideimides produced by various of these processes are more readily manufactured and fabricated than the polyimides, the ester or similar groups introduced provide a weak point in the resistance of the molecule to hydrolysis and oxidation at elevated temperatures. These disadvantages are discussed at length in "New Linear Polymers" by Lee, Stoffey and Neville (McGraw-Hill, 1967) and the different properties of the various types of "hinge" elements are discussed in "Polyimides" by Adrova, Bessoner, Lains and Rudakov (Technomic Publishing, 1970), which are incorporated by reference to illuminate the background of the present invention. French Pat. No. 1,565,700 (CA 71, 10154g) suggests a protracted route to bis-anhydrides via Friedel-Crafts reaction of o-xylene and the mononuclear reactant terephthaloyl chloride. Kogyo Kagaku Zaashi 69, 1069 (1967) (CA 68, 69435s) is similar, save that p-bis (chloromethyl) benzene is employed. Oxidation yields the dianhydride and, in the latter case, the ketone functions.

BRIEF SUMMARY OF THE INVENTION

According to this invention there are provided, by a new use of the Friedel-Crafts reaction, novel bis-anhydrides derived from materials like tri-mellitic anhydride which are free of the oxidation-vulnerable ester groups which have characterized previous bis-anhydrides so formed. The process of the invention is far less laborious than those previously employed in forming ketone-supplied bis-anhydride monomers (e.g., French Pat. No. 1,565,700 supra) and does not require polynuclear diacyl halides whose general unavailability prohibits economic extension of the process of that patent to the production of polynuclear compounds like those of the present invention. The novel bis-anhydrides of this invention are suitable, inter alia, for use as reactants or co-reactants in polyimide manufacture and such polyimides form a part of this invention.

Accordingly, this invention provides compounds of formula

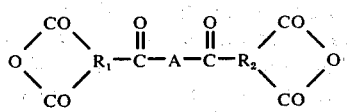

where $R_1$ and $R_2$ are trivalent aromatic radicals having vicinal carbon atoms (for example, 1,2-positions in benzene, 1,2- or 1,8- positions in naphthalene, etc.) from which depend the valence bonds to which the anhydride moieties are attached, and where A is a divalent polynuclear aromatic radical whose valence bonds stem from nuclear carbon atoms, preferably on separate nuclei.

$R_1$ and $R_2$ can be selected from the group consisting of phenyl, naphthyl or biphenyl and A can be a divalent polynuclear aromatic selected from the group consisting of diphenyl-Z, dinaphthyl-Z, dibenzofuran, fluorene, $C_1$ to $C_3$ alkylidene fluorene, carbazole and dibenzothiophene wherein Z is O, S, $C_1$ to $C_3$ alkylidene or a single valence bond, and the point of attachment to the trivalent aromatic radicals of the carbonyl bridges between the trivalent and divalent aromatic radicals being other than ortho to the vicinal carbon atoms.

The invention also provides a process for the manufacture of such compounds which comprises treating a suitable derivative of an aromatic tricarboxylic acid, in which two carboxyl groups are bound to adjacent carbon atoms, preferably the monoanhydride monoacid chloride, with a polynuclear aromatic compound under Friedel-Crafts reaction conditions.

That useful monomeric products can be produced by this process is surprising, especially in view of the teaching of British Pat. No. 1,019,226 in which certain of the starting materials used in the present invention are caused to react in the presence of $AlCl_3$ to yield polyketones. In an example in that patent, pyromellitic anhydride and diphenyl ether react in the presence of aluminum chloride to yield a copolymer of poly(4,6-dicarboxy isophthaloyl diphenyl ether) and poly(2,5-dicarboxy terephthaloyl diphenyl ether), and formulae given in the text would require that the corresponding reaction with the anhydride/chloride of trimellitic acid yield a copolymer of 2-carboxy isophthaloyl diphenyl ether and 2-carboxy terephthaloyl diphenyl ether.

DETAILED DESCRIPTION OF THE INVENTION

As the tricarboxylic acid component, there may be employed suitable derivatives, as for example the monoanhydride monoacid chloride of various tricarboxylic acids. As suitable acid derivatives there may be mentioned, e.g., 4-chloroformylphthalic anhydride, the acid chloride of the 1,8-anhydride of 1,2,8- or 1,3,8- or 1,4,8-naphthalenetricarboxylic acid, 3-chloroformylphthalic anhydride, 3[o-chloroformylphenyl]phthalic anhydride, the acid chloride of the 2,3-anhydride of 2,3,6-naphthalone tricarboxylic acid, 3[o-chloroformyl benzoyl]phthalic anhydride, and 4[p-chloroformylphenoxy]phthalic anhydride. Other suitable derivatives include other acid halides and compounds in which the anhydride moiety is replaced, e.g., by the sulfide (as by reacting the anhydride with sodium sulfide) or by substituted imide in which the substituent may be, for example, an alkyl group such as ethyl or butyl. The imides can be prepared, e.g., by reacting the monoanhydride of the tricarboxylic acid successively with alkyl amine and thienyl chloride.

Although the above methods will ultimately yield the bis-anhydrides of this invention, it is to be understood that the preferred route to the synthesis of the bis-anhydrides is to react acid halide-anhydrides directly with the polynuclear aromatic compounds.

As the aromatic compound there may be employed any polynuclear compound having at least two nuclear carbons available for substitution. Mononuclear compounds are quite susceptible to deactivation upon monosubstitution, and are not employed in the invention. Where a single reaction product is desired, there are preferably only two available nuclear carbons or two carbons which are substantially more reactive than other available carbons. Preferably, the potential substitution sites are activated by other substituents in the molecule and preferably the molecule is free from substituents which deactivate these sites. Thus, molecules containing alkyl or alkoxy substituents appropriately located will be more, and molecules containing nitro or nitrile groups will be less, reactive than unsubstituted compounds. It will of course be appreciated that substituents which favor or retard the electrophilic substitution associated with the Friedel-Crafts reaction may or may not be desirable in the final product, for example the polyimide, for which the bis-anhydride is generally prepared. It will also be appreciated that the molecule should not contain substituents or linkages which will interfere with the reaction, be split or released under the reaction conditions, etc. Those skilled in the art are readily able to decide whether a particular compound will or will not be a suitable starting material, the same considerations being applicable both to the aromatic compound and to the tricarboxylic acid derivative, mutatis mutandis.

As examples of suitable aromatic compounds there may be mentioned biphenyl, diphenyl ether, 2,2-diphenylpropane, dibenzyl, fluorene, dibenzofuran, anthracene, diphenyl sulphide, bis(phenoxymenthyl)-cyclohexane, bi-α-naphthyl, di-β-naphthyl, di-α-napht-hyl ether, di-β-naphthyl ether, di-α-naphthyl sulfide, di-β-naphthyl sulfide, dibenzo-p-dioxin, diphenylmethane, carbazole, dibenzothiophene, naphthalene, phenanthrene, perylene, picene, chrysene, indene, acridine, bisphenoxybenzene, or terphenyl.

At least about two molar equivalents of the tricarboxylic acid derivative are employed per molar equivalent of the polynuclear reactant, this stoichiometry favoring bis-anhydride formation rather than formation of carboxy phthaloyl polymers like those of the aforementioned British patent.

Those skilled in the art can readily determine Friedel-Crafts catalysts optimal for reaction between a particular aromatic compound and tricarboxylic acid derivative and what quantities of catalyst are best. However, without wishing to be bound in any way by the theoretical discussion which follows, it is believed that the following guidelines for choice of catalyst and quantity will be of assistance.

With Lewis acid catalysts (L) the reaction of the invention proceeds through the formation of an exo-carbonium complex (A) and/or a covalent donor-acceptor adduct (B).

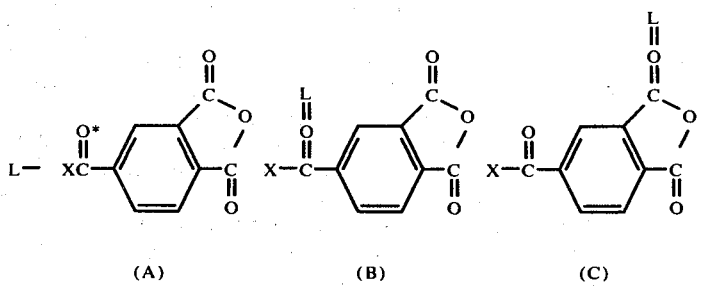

(A)  (B)  (C)

The principal undesired reaction, acylation by the anhydride group, proceeds through a donor-acceptor coordination complex of the Lewis acid with the anhydride group (C), resulting in a direct attack by an aromatic substrate on the anhydride end of the molecule, or opening of the anhydride ring to an acid halide or both. Those catalysts whose halide-ion affinity is greater than their oxygen coordination affinity are preferred as favoring formation of complex A and, of course, those having great halide-ion affinity and low oxygen coordination affinity are most preferred.

Addition of an excess of catalysts like aluminum chloride, which itself exhibits relatively great oxygen affinity and is hence not preferred, is to be avoided as encouraging acylation by the anhydride group. For example, from a stoichiometric standpoint, but one molecular equivalent of aluminum trichloride is required for Friedel-Crafts reaction through the acyl chloride group, whereas it is known that two are required to acylate with phthalic anhydride per se. Use of aluminum chloride in excess of that required for bis-anhydride formation, then, is to be avoided as encouraging acylation by the anhydride moiety. It will also be appreciated, of course, that for a particular compound acylation by the anhydride moiety is encouraged at higher and discouraged at lower temperatures.

What determines whether all or less than the stoichiometric amount of catalyst is preferred is the degree of dissociation of the coordination complex between the Lewis acid and aromatic ketone formed in the Friedel-Crafts reaction. A reaction yielding a highly stable complex (inactive as a Friedel-Crafts catalyst) requires a stoichiometric amount of the Lewis acid to go to completion. A Lewis acid possessing small affinity for oxygen will form a weak ketone complex that will be appreciably dissociated (to the free Lewis acid and ketone) affording more active catalyst and allowing the reaction to proceed to completion with less than the stoichiometric amount of catalyst present.

Those strong Lewis acids that yield an appreciably dissociated complex with the aromatic ketone (carbonyl) formed on monoacylation will also lead to diacylation, with the reaction proceeding mainly through the less deactivated (by electron withdrawal) free ketone.

The following moderate-to-strong Lewis acids and precursors (among others) are suitable when used in (1) much less than stoichiometric amounts [≈0.005:1 mole ratio to a difunctional aromatic substrate, at about 150°–250° C, in melt form or solution (sulfolane, etc)] up to (2) stoichiometric amounts [(0.5-3):1 mole ratio to a difunctional aromatic substrate, at about 40°–120° C, generally in solution (PhNO$_2$, sulfolane, chlorobenzenes, etc.)]: AsF$_5$; AuBr$_3$, -Cl$_3$; FeBr$_3$, -Cl$_3$; GaBr$_3$, -Cl$_3$; HfCl$_4$; InBr$_3$, I$_3$; MoCl$_5$; NbBr$_5$, -Cl$_5$, -F$_5$; ReBr$_3$, Cl$_3$; SbCl$_5$, -F$_5$; SnBr$_4$, -Cl$_4$, -F$_4$; TaBr$_5$, -Cl$_5$, -F$_5$; TeCl$_2$, -Cl$_4$; TiBr$_4$, -Cl$_4$ -F$_4$; VCl$_4$; WCl$_6$; ZrBr$_4$, -Cl$_4$. With appropriate acyl halides, catalytic amounts of the free metals, metal complexes or metal oxides may be employed as well, in which case the active halide catalyst is generated during reaction by the produced halide acid. The conditions specified have been found especially suitable for the disubstitution of difunctional aromatic substrate subject to a degree of deactivation by monosubstitution (e.g., biphenyl and phenyl ether). Active difunctional aromatic compounds not significantly deactivated on monosubstitution (e.g., p-diphenoxybenzene and dibiphen-4-ylmethane) can be disubstituted at lower temperatures [about 0°–50° C for (0.5-3):1 mole ratios (catalyst to aromatic substrate) and at about 90°–150° C for about 0.005:1 mole ratios].

The following weak Lewis acids or precursors can be used in much less than stoichiometric amounts (or higher) at about 190°–250° C for diacylation of only those active aromatic compounds not significantly deactivated on monosubstitution: AsBr$_3$, -Cl$_3$, -F$_3$; BBr$_3$ -F$_3$, -I$_3$; BeBr$_2$, -Cl$_2$; BiBr$_3$, -Cl$_3$; CeCl$_3$; CoBr$_2$, -Cl$_2$; CrBr$_3$; CuBr, -Cl, Br$_2$, -Cl$_2$; FeBr$_2$, -Cl$_2$; HgBr$_2$, -Cl$_2$; ICl, -Cl$_3$, -I; MgBr$_2$; PF$_5$; SbBr$_3$, -Cl$_3$; SiCl$_4$, -F$_4$; TeBr$_4$; ThCl$_3$; TlCl$_3$; UCl$_4$; ZnBr$_2$, -Cl$_2$, -I$_2$.

Finally, the following Bronsted acid types of Friedel-Crafts catalysts can also be used in conjunction with the free carboxy group-containing anhydrides: polyphosphoric acid or trifluoromethanesulfonic acid. With these catalysts the reaction proceeds through the mixed anhydride, e.g.

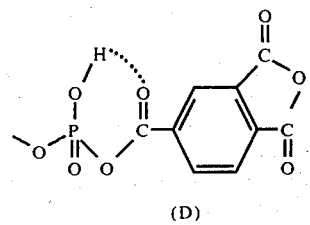

(D)

They are approximately comparable in activity to the weak Lewis acids listed above. There should be present in the reaction mixture at least about two moles of tricarboxylic acid derivative for each mole of aromatic compound; advantageously the ratio is within the range of about 2.0:1 to about 4:1, preferably about 2.1:1 to about 3:1. The reaction conditions can be any of those normally employed in Friedel-Crafts acylations.

If desired or required, the resulting bis-anhydrides may be purified by recrystallization. Suitable recrystallization solvents are given in the examples. It will be appreciated that from the bis-anhydrides or tetraacids there may be made a wide range of derivatives.

It is possible and in certain circumstances desirable to employ a mixture of two or more tricarboxylic acid derivatives, a mixture of two or more aromatic compounds, or mixtures of both reactants. This technique may be used, for example, where commercially available materials are mixtures of isomers, or where the desirable properties of two or more starting materials may be advantageously combined. Allowance for differing reactivities of materials should, of course, be made.

It is also possible to carry out the reaction stopwise, in which case a tribasic acid derivative and an aromatic compound can be admixed in approximately equimolar quantities, then a second molar quantity of acid derivative added and the reaction continued at a higher temperature. It will be appreciated that the second molar quantity may be the same or a different acid derivative; in the latter case a mixed bis-anhydride is readily formed.

The novel bis-anhydrides can be incorporated into polyimides by reaction, by methods known per se, with diamines. The novel bis-anhydrides can constitute the only bis-anhydride present in the reaction mixture or they can have as coreactants known bis-anhydrides. Such known bis-anhydrides, diamines and typical reaction conditions are described in ample detail in the patents and literature referred to above.

The invention is further illustrated by reference to the following examples, in which all parts and percentages are by weight and all temperatures in degrees Centigrade unless otherwise stated.

EXAMPLE 1

A melt of 636.8g (3.03 mole) 4-chloroformylphthalic anhydride and 203.0g (1.32 mole) biphenyl was stirred under nitrogen for 25 minutes at 200°–210° C while adding 11.7g (0.072 mole) ferric chloride. After a further 15 minutes at the same temperature, the reaction mixture was cooled, crushed, boiled with 10% acetic acid containing some pyridine and filtered warm. After boiling the filter cake with 70% acetic acid, cooling and filtering, 347.36g of 4,4''-bis(benzophenone- 3',4'-dicarboxylic acid) were obtained, representing a 49% yield. After heating at 210° C under vacuum, the corresponding anhydride, m.p. 300.5°–302.5° C was obtained. Recrystallization from 90% acetic acid containing pyridine and again heating at 210° C under vacuum gave 275.35g (41.7%) of anhydride, m.p. 302.0°–303.5° C. A further recrystallization (from acetic acid-water containing some pyridine) and cyclization gave a melting point of 304.0°–305.5° C. Analysis: % carbon, hydrogen (theoretical values in parentheses) 71.70, 2.81 (71.72, 2.69).

EXAMPLE 2

A solution of 3.40g (0.02 mole) phenyl ether in 8 ml nitrobenzene was added dropwise over a period of 24 minutes to a stirred solution of 9.68g (0.046 mole) 4-chloroformylphthalic anhydride and 6.80g (0.042 mole) ferric chloride in 30 ml nitrobenzene maintained at 22°–43° C under nitrogen. The reaction mixture was heated at 100° C for 10 minutes, cooled on ice, shaken with dilute sodium bicarbonate, acidified with hydrochloric acid, stirred with an excess of ether and filtered. The filter cake was heated at 205° C under vacuum, extracted with hot xylene and the extract cooled. 4.00g (38.8%) of yellow crystals of 4,4''-oxybis(benzophenone-3',4'-dicarboxylic acid) dianhydride were recovered after drying under vacuum at 170° C, which melted at 210°–212° C. After recrystallization from xylene the pale yellow crystals melted at 214.5°–215.5° C. Alternative recrystallization solvents were o-dichlorobenzene, tetralin and acetic anhydride. Analysis: % carbon, hydrogen 69.62, 2.83 (69.50, 2.72).

EXAMPLE 3

0.12g (7.4 × 10$^{-4}$ mole) ferric chloride was added over 5 minutes to a stirred melt of 4.42g (0.021 mole) 4-chloroformylphthalic anhydride and 1.96g (0.01 mole) 2,2-diphenylpropane maintained at 199°–201° C under nitrogen. The reaction mixture was heated at 201°–205° C for 10 further minutes, cooled, crushed, boiled with water containing some pyridine and cooled again. The aqueous phase was decanted from the resulting viscous mass of 4,4''-isopropylidenebis(benzophenone-3',4'-dicarboxylic acid). The crude acid was heated in vacuo at 205° C to form the anhydride which was boiled in xylene, cooled, decanted, and heptane was added to the resulting solution. The precipitate was recrystallized from acetic anhydride yielding 0.92g (16.9%) of anhydride, m.p. 216.5°–219° C. A second recrystallization yielded off-white crystals m.p. 219.5°–221.0° C. Analysis: % carbon, hydrogen 72.29, 3.64 (72.79, 3.70).

EXAMPLE 4

0.07g (4.3 × 10$^{-4}$ mole) ferric chloride was added during 4.5 minutes to a stirred melt of 4.42g (0.021 mole) 4-chloroformylphthalic anhydride and 1.82g (0.01 mole) bibenzyl maintained at 198°–209° C under nitrogen. After 6.5 minutes further heating at 207°–208° C, the reaction mixture was treated as described in Example 3 to recover the crude 4,4''-ethylenebis(benzophenone-3',4'-dicarboxylic acid) which was crystallized from 10% acetic acid, 1.16g (20.5%) of the product acid were recovered. Cyclization at 210° C under vacuum yielded 1.02g (19.2%) of the anhydride, m.p. 262°–266° C. Recrystallization from o-dichlorobenzene yielded crystals melting at 265°–267° C. Analysis, % carbon, hydrogen 72.43, 3.48 (72.45, 3.42).

EXAMPLE 5

1.0g (6.17 × 10$^{-3}$ mole) ferric chloride was added to a stirred melt of 44.2g (0.21 mole) 4-chloroformylphthalic anhydride and 16.6g ($\approx$0.10 mole) fluorene, technical grade, at 190°–192° C maintained under nitrogen. The addition of ferric chloride was made over a period of 7 minutes after which the reaction mixture was maintained for a further 8 minutes at 180°–185° C, cooled, crushed, boiled with pyridine-containing water, cooled and filtered. The filter cake was recrystallized from 70% acetic acid containing a small quantity of pyridine, filtered, washed with more 70% acetic acid and then with water. Cyclization at 210° C in vacuo yielded 10.65g (20.8%) of crude 4,4'' (fluorene-2',7'-dioyl)-diphthalic acid dianhydride. Recrystallization twice from o-dichlorobenzene followed by recrystallization from benzonitrile yielded 7.25g (14.1%) product, m.p. 276.5–278.5%. Analysis: % carbon, hydrogen 72.20, 2.65 (72.38, 2.74).

EXAMPLE 6

In a manner similar to that described in Example 3, 4,4''(dibenzofuran-3',6'-dioyl) diphthalic acid and the corresponding dianhydride were manufactured from dibenzofuran. After recrystallization from benzonitrile, the anhydride yielded off-white crystals, m.p. 334°–337° C, yield 8.3%. Analysis: % carbon, hydrogen 69.87, 2.39 (69.77, 2.34).

EXAMPLE 7

In a manner similar to that described in Example 3, 4,4''(anthracene-9',10'-dioyl) diphthalic acid and the corresponding dianhydride were manufactured from anthracene. Recrystallization of the anhydride from acetic anhydride gave a yield of about 7.0% of the anhydride, m.p. 330°–334° C. Analysis: % carbon, hydrogen 72.85, 2.54 (73.01, 2.68).

EXAMPLE 8

5.0245g (0.01 mole) 4,4''-bis(benzophenone-3',4'-dicarboxylic acid) dianhydride, was added to a solution of 2.0024g (0.01 mole) 4,4'-oxydianiline and 0.0444g (0.003 mole) phthalic anhydride in 90 ml M-methylpyrrolidone and the mixture heated to about 40° C. The dianhydride dissolved slowly during the course of an hour. After about 2 hours, a further 0.0502g (0.0001 mole) of dianhydride was added to make up for observed insoluble portions of the original quantity. After a further 30 minutes heating at 40° C, the solution was raised to 190° C and maintained at that temperature for 4 hours to bring about imidization. The hot solution was diluted with a further 90 ml N-methylpyrrolidone and cooled. The polymer was precipitated by mixing with ether, filtered and washed successively with water, methanol and ether. The powder was then dried under vacuum at 90° C for 2 hours, heated for a few minutes at 270°–280° C, and then pressed into a slab at 310° C. The inherent viscosity (0.1g/100 ml sulphuric acid) was 1.37, tensile strength 12,455 psi, elongation 5–10%. The glass transition temperature, Tg, was 240° C. The glass transition temperatures in this and subsequent examples were obtained by plotting the change in shear modulus of the polymer with temperature rise. The midpoint of the rapid drop in modulus with temperature rise is taken as the Tg.

EXAMPLE 9

In a manner similar to that described in Example 8, a polyimide was prepared from 4,4''-oxybis(benzophenone-3',4'-dicarboxylic acid) dianhydride (0.985 molar ratio), oxydianiline (1.000 molar ratio) and phthalic anhydride (0.03 molar ratio). Analysis: % carbon, hydrogen 73.22, 3.25. Theoretical for 1:1 molar ratio of dianhydride and diamine, 73.90, 3.25. The inherent viscosity (0.1g/100 ml sulphuric acid) was 1.96, while the glass transition temperature was about 235° C.

EXAMPLE 10

In a manner similar to that of Example 8, a polyimide was prepared from 4,4''-bis(benzophenone-3',4'-dicarboxylic acid) dianhydride (1.00 molar ratio) and m-phenylenediamine (1.00 molar ratio) with phthalic anhydride (0.01 molar ratio) as capping agent. The polymer had an inherent viscosity of 0.88 (0.0589/100 ml sulphuric acid, 25° C). Analysis: % carbon, hydrogen, 75.25, 3.26 (theoretical, for 1:1 molar ratio dianhydride: diamine - 75.26, 3.16), glass transition temperature about 280° C.

EXAMPLE 11

To a stirred solution (under $N_2$) of 4.25g (0.0393 mole) m-phenylene diamine (m.p. 62.4°–64.2° C) in 50 ml N-methylpyrrolidone (NMP) at 25° C, was slowly added a solution of 0.857g (0.00393 mole) pyromellitic dianhydride and 17.77g (0.0354 mole) 4,4''-bis(-benzophenone-3',4'-dicarboxylic acid anhydride) (m.p. 302°–3.5°) in 150 ml NMP over a period of 20 minutes and residues washed in with 25 ml more NMP. The reaction mixture was maintained at 25°–29° C during the addition and allowed to cool with stirring to 25° C over a period of 1 hour, followed by addition of 0.058g (0.039 millimoles) of phthalic anhydride. After stirring at 25° C for 1 hour 40 minutes longer, the reaction mixture was heated to 174° C over a period of 11 minutes, and maintained at 174° C for 1 hour, followed by cooling, and addition to 400 ml anhydrous methanol with stirring in a Waring Blender. The resulting precipitate was washed thoroughly with more methanol and dried at 200°–225° for 3 hours yielding 21.53g of yellow powder of inherent viscosity 0.59. The material, as a 0.5% concentration in $H_2SO_4$, dissolved after 46 hours at 25° C, followed by 5.5 hours at 40° C. A minor portion of precipitate remained.

What is claimed is:

1. A compound of the formula

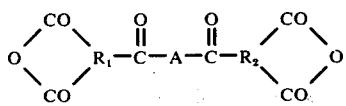

wherein $R_1$ and $R_2$ are trivalent aromatic radicals having vicinal carbon atoms from which stem the valence bonds to which the anhydride moieties are attached and selected from the group consisting of phenyl and naphthyl and A is a divalent polynuclear aromatic selected from the group consisting of naphthalene anthracene, diphenyl-Z, dinaphthyl-Z, dibenzofuran, fluorene, carbazole, and dibenzothiophene wherein Z is O, S, $C_1$ to $C_3$ alkylidene or a single valence bond, the point of attachment to said trivalent aromatic radicals of the carbonyl bridges between said trivalent and divalent aromatic radicals being other than ortho to said vicinal carbon atoms.

2. The compound of claim 1 wherein $R_1$ and $R_2$ are

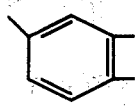

3. The compound of claim 1 wherein $R_1$ and $R_2$ are identical.

4. The compound of claim 1 wherein $R_1$ and $R_2$ are naphthyl selected from the group consisting of

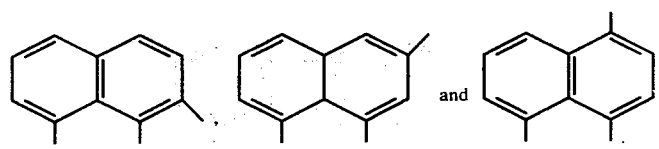

5. The compound of claim 1 wherein A is

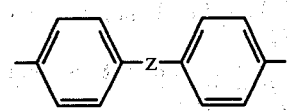

in which Z is O, S, $C_1$ to $C_3$ alkylidene or a single valence bond.

6. The compound of claim 1 wherein A is selected from the group consisting of

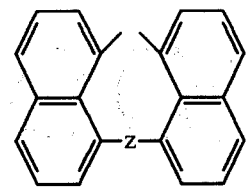

or

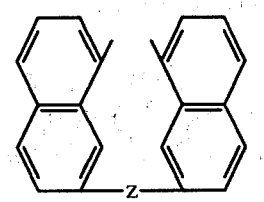

in which Z is O, S, $C_1$ to $C_3$ alkylidene or a single valence bond.

7. The compound of claim 1 wherein A is selected from the group consisting of

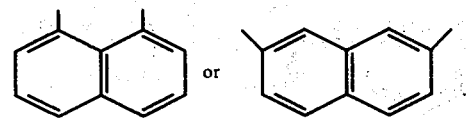

8. The compound of claim 1 wherein A is

9. The compound of claim 1 wherein A is selected from the group consisting of in which Y is NH, O, or S.

10. The compound of claim 1 wherein A is 4',4'-biphenylylene.

11. The compound of claim 1 wherein A is 4,4'-oxybisphenylene.

12. The compound of claim 1 wherein A is 4,4'-isopropylidenebisphenylene.

13. The compound of claim 1 wherein A is 4,4'-ethylenebisphenylene.

14. The compound of claim 1 wherein A is 2,7-fluorenylene.

15. The compound of claim 1 wherein A is 3,6-dibenzofuranylene.

16. A compound of formula

17. A compound of formula wherein X is selected from the group consisting of a valence bond, oxygen, sulfur or $C_1$–$C_3$ alkylene.

18. A compound of formula

19. A process which comprises the reaction, in the presence of a Friedel-Crafts catalyst, of at least two molar equivalents of at least one aromatic tricarboxylic acid derivative selected from the group consisting of (a) $X-\overset{O}{\underset{\|}{C}}-R_1\overset{CO}{\underset{CO}{\diagup\diagdown}}O$ and $X-\overset{O}{\underset{\|}{C}}-R_2\overset{CO}{\underset{CO}{\diagup\diagdown}}O$ where $R_1$ and $R_2$ are trivalent aromatic radicals having vicinal carbon atoms from which stem the valence bonds to which the anhydride moieties are attached and selected from the group consisting of phenyl and naphthyl, and wherein X is halogen, the point of attachment to said trivalent aromatic radicals of the carbonyl bridge between said trivalent aromatic radical and said halogen being other than ortho to said vicinal carbon atoms, with one molar equivalent of a compound of formula (b) H-A-H wherein A is a divalent polynuclear aromatic selected from the group consisting of naphthalene anthracene, diphenyl-Z, dinaphthyl-Z, dibenzofuran, fluorene, carbazole, and dibenzothiophene wherein Z is O, S, $C_1$ and $C_3$ alkylidene or a single valence bond to produce a compound of formula $O\overset{CO}{\underset{CO}{\diagdown\diagup}}R_1-\overset{O}{\underset{\|}{C}}-A-\overset{O}{\underset{\|}{C}}-R_2\overset{CO}{\underset{CO}{\diagup\diagdown}}O$ wherein the point of attachment to said trivalent aromatic radicals of the carbonyl bridges between said trivalent and divalent aromatic radicals being other than ortho to said vicinal carbon atoms.

20. The process of claim 19 wherein said catalyst is ferric chloride.

21. The process of claim 19 wherein said reaction is carried out in the molten state.

22. The process of claim 19 wherein the molar ratio $a:b$ lies within the range from about 2:1 to about 4:1.

23. The process of claim 19 wherein $R_1$ and $R_2$ are identical and wherein the valence bonds of A are contained in separate nuclei.

24. The process of claim 19 wherein $R_1$ and $R_2$ are selected from the group consisting of phenyl or naphthyl and A is selected from the group consisting of anthracene, diphenyl-Z, dinaphthyl-Z, dibenzofuran, fluorene, carbazole and dibenzothiophene wherein Z is O, S, or a single valence bond.

* * * * *